United States Patent [19]

Vegezzi

[11] 4,199,585

[45] Apr. 22, 1980

[54] METHOD AND COMPOSITION FOR THE THERAPY OF CEREBRAL CIRCULATORY DISEASES

[76] Inventor: Davide Vegezzi, Via Cabione, 1, Massagno (Lugano), Switzerland

[21] Appl. No.: 888,978

[22] Filed: Mar. 22, 1978

Related U.S. Application Data

[63] Continuation-in-part of Ser. No. 770,501, Feb. 22, 1977, abandoned.

[51] Int. Cl.² .............................................. A61K 31/475
[52] U.S. Cl. ...................................................... 424/262
[58] Field of Search ......................................... 424/262

[56] References Cited

PUBLICATIONS

Cory: Mora–Chem. Abst., vol. 87, (1977), p. 172,914p.

*Primary Examiner*—Sam Rosen
*Attorney, Agent, or Firm*—Haseltine, Lake & Waters

[57] ABSTRACT

The invention relates to a method and a therapeutic composition for the treatment of cerebral circulatory diseases by administration of vincamine as the active ingredient wherein particular hematic levels are ensured in order to maintain the therapeutic action. More particularly, delayed-release compositions are specially provided.

3 Claims, No Drawings

METHOD AND COMPOSITION FOR THE THERAPY OF CEREBRAL CIRCULATORY DISEASES

This application is a continuation-in-part of U.S. patent application Ser. No. 770,501 filed on Feb. 22, 1977, now abandoned.

The present invention relates to a method and a therapeutic composition for the treatment of cerebral pathologic conditions deriving from several factors of circulatory nature and, more particularly, from phenomena of circulatory insufficiency of thrombotic or arteriosclerotic type.

The use of the vincamine for treatment of these pathologic conditions is already known, such a use being based on the vasodilating effect of the level of the cerebral network thereof, which is related to a specific vasodilating action which permits the blood requirements to be better adapted to the metabolic needs of the brain. The action of vincamine is also carried out through a metabolic activity involving an enhanced respiratory activity of the nervous cells, especially when subjected to pathologic conditions.

The treatment by vincamine is effected either orally or by the parenteral route; for reasons of local and general tolerability and due to pharmacokinetic causes the daily dosage must be fractionated into well defined time intervals (every 8 or 12 hours).

The daily dosage is consequently comprised between 60 and 80 mg. per os and between 15 and 45 mg. per intramuscular or intravenous route.

It is furthermore important to point out that, although by parenteral administration some alterations due to circulatory disease (vasospasms) can be treated in the acute phase, the oral administration, in order to achieve an efficacious action in the cerebral pathologic conditions the chronic type (arteriosclerosis, post-thrombotic conditions, etc.), requires a prolonged treatment of about 20 to 30 days.

However, in the case of the continued treatments, a discontinuity of the therapeutic effect occurs, whereby the therapeutic action is reduced, especially during the first days of administration of the drug, to time periods well defined and limited after the administration.

The use of therapeutic compositions, which contained vincamine, in the form of the free base or the hydrochloride and in delayed-release formulations, has been suggested, for example by the French Patent Specification No. 2,253,507, filed on Dec. 11, 1973: unit dosages in the range from 20 to 60 milligrams of vincamine base were recommended. The U.S. Pat. No. 3,957,981, of May 18, 1976 discloses pharmaceutical compositions of vincamine and acetylsalicylic acid. The hematic levels which are obtained with compositions such as those disclosed by the prior art above indicated do not appear, however, to be fully satisfactory for certain therapeutic requirements.

With respect to the oral administration pharmacokinetic research work has therefore been carried out, by the present applicant, both on test animals and humans, in order to assess the relationship between the oral administration of the vincamine, the absorption at the gastroenteric level, the hematic concentrations, the concentrations in the cerebral tissues and the elimination rate of the drug. These researches have been carried out by a multicompartmental system and by using the least-square differences.

More specifically the research work aimed to establish:

(a) the relationship between the hematic levels and the concentrations in the cerebral tissue;

(b) the cerebral "threshold" concentration capable of causing a pharmacological or metabolic effect;

(c) the hematic levels within which the pharmacotherapeutical activity of the vincamine occurs.

From the results of such a research work it was surprisingly found that, in both rats and men, the pharmacological activity of the vincamine is obtained at two levels of hematic concentrations.

More particularly, as regards the metabolic activity of vincamine, it has been found and it is the subject-matter of the present invention that such an activity is ensured with continuity by maintaining in men a hematic level of between 0.1 and 0.3 $\mu$g/ml. corresponding to a cerebral concentration, as obtained by mathematical-statistical extrapolation, of between 0.2–0.6 $\mu$g/g.

Such a finding was already preceded by analogous tests carried out on the rat, hematic levels of between 6 and 12 $\mu$g/ml, corresponding to concentrations of 4 to 11 $\mu$g/g. of cerebral tissue, having been then determined.

More particularly, in the case of the rat, reference was had to the favorable influence of vincamine on the tests of conditioning and of behavior, whereas in the case men, reference was made to the improvement of memory, attention and learning capability, as evaluated through psychometric and intelligence quotient tests.

With respect to the pharmacological and therapeutic activity connected to the vasodilating activity at the cerebral level, it has been found, that which constitutes another feature of the present invention, that it is necessary to maintain in men a hematic concentration of 0.2–0.5 $\mu$g/ml, corresponding, on the basis of the same determination method, to a vincamine concentration in the cerebral tissue of between 0.8 and 1.6 $\mu$g/g. of cerebral tissue.

In this case, also, the preliminary tests on the laboratory animals gave hematic concentrations of 12 to 25 $\mu$g/ml.

The activities of this second type have been tested in rats through the microcirculation test and in men by means of angioscintigraphic techniques.

Thus, as a definition, the present invention provides a therapeutic method for the treatment of cerebral pathologic conditions through the administration of vincamine characterized in that the drug is administered in dosages such as to maintain:

(a) with reference to the achievement of metabolic effect, a hematic concentration of 0.1 to 0.3 $\mu$g/ml, and (b) with reference to the achievement of a central vasodilating action, a hematic concentration of 0.2 to 0.5 $\mu$g/ml.

According to the preferred embodiment and for a general therapeutic use the present invention provides the administration of vincamine per oral route in a dosage such as to maintain a hematic level of at least 0.2 $\mu$g/ml.

From the preceding considerations it is evident that one of the essential conditions for the success of the therapeutic method according to the present invention resides in maintaining some hematic levels constant. Of course, this can be ensured by properly dividing the daily administrations or, better, their frequency, or, preferably, by having recourse to one of the well known pharmaceutical formulations with delayed and fractionated release.

The present invention is also characterized in that it provides a therapeutic composition containing vincamine, wherein the active substance is formulated so as to ensure a delayed release, said release being such as to maintain the aforesaid hematic levels.

The experimental work has furthermore permitted to ascertain that the practical application of the method and thus of the therapeutic compositions according to the present invention permits, the therapeutic action being the same, the use of dosages definitely lower than those conventionally admitted, with conspicuously apparent advantages.

On the basis of the previously stated considerations, that is, that of the constant hematic levels which must be maintained in the patient undergoing the therapy, it will be easy to determine the dosages of the pharmaceutical preparations, these dosages being moreover necessarily depending on a selected posology as well as on the toxicity limits. The latter, vincamine being a compound well known in the pharmaceutical art and studied and investigated for a long time, are already well known in this field of the art.

As regards the preferred embodiment of the therapeutic composition according to the present invention, it is, as outlined above, the delayed- and programmed-release composition.

A predetermined unit amount of vincamine and/or vincamine hydrochloride is coated so as to cause a programmed release up to 24 hours from the administration. This result is obtained by coating the starting material with a lipidic layer formed by glycerol esters of fatty acids or by hydrogenated vegetable oils, either alone or in combination with ethyl cellulose, or by alkalies and fatty acids.

The coating may form up to 50% of the final weight of the pharmaceutical unit.

The same delayed release is achieved by granulated preparations in which the active substance is encapsulated in a matrix formed by carbowax - ethyl cellulose or hydroxypropylcellulose, metasilicic polymers, polyvinyl chloride and acetate, styrene-maleic acid copolymers, natural rubber, either alone or in mixtures, together with inert fillers.

On the basis of the weight ratio of the active substance to the coating needed to bring about the desired release rating, the nature and the proportions of the coating can be determined.

The granulated formulations are prepared by means of conventional procedures (granulation, melting, mixing, etc.), and are utilized for the preparation of tablets, capsules, dragees, as well as liquid suspensions.

Therapeutic compositions with delayed release of the active principle have been prepared according to the following examples.

EXAMPLE 1

100 mg. of vincamine or its hydrochloride are intimately admixed with 10 mg of Eudragit RL-PM and 20 mg of Eudragit RS-PM (Eudragit RL-PM and RS-PM being the trade names of proper acrylic resins sold by Rohm & Haas Co.), after sieving through a 200 mesh/sq.cm sieve; the mixture is kneaded with 5 parts by weight of methylene chloride, until a mass having elastic consistency is obtained. The mass is granulated and passed through a 4 mesh/sq.cm sieve and dried in a ventilated drier.

The dried granulate is regranulated on a 36 mesh/sq.cm sieve and then converted into tablets, in the conventional way, with the following compositions:

|  | Composition | |
| --- | --- | --- |
|  | A | B |
| Vincamine (mg) | 75 | 25 |
| Eudragit mixture, mg | 22.5 | 22.5 |
| Calcium phosphate, mg | 88.5 | 45.5 |
| Talc, mg | 9 | 4.5 |
| Magnesium stearate, mg | 5 | 2.5 |
| Ethocel, mg | — | — |
|  | 200 | 200 |

The in vitro release was measured by the test apparatus Sartorius SM 16750 with the following results:

|  |  | Composition | |
| --- | --- | --- | --- |
|  |  | A | B |
| Release after | 1 hour | 18.2% | 20% |
| " | 2 hours | 39.7% | 40% |
| " | 3 hours | 50.2% | 50% |
| " | 4 hours | 65% | 70% |
| " | 6 hours | 75% | 85% |

EXAMPLE 2

15 parts of ETHOCEL 20-SE (ethyl cellulose) are dissolved in 40 parts of methylene chloride, and the solution is supplemented, with stirring, by 100 parts by weight of vincamine base or hydrochloride until a homogeneous granulate is obtained. The granulate is sieved through a 4 mesh/sq.cm sieve and dried in a drying cabinet until the solvent is completely evaporated. The granulate is regranulated through a 36 mesh/sq.cm sieve and used for the preparation of tablets having the following composition:

|  | Composition | | |
| --- | --- | --- | --- |
|  | C | D | E |
| Vincamine, mg | 75 | 50 | 25 |
| ETHOCEL, mg | 11.25 | 7.5 | 3.75 |
| Calcium phosphate, mg | 99.75 | 128.5 | 64.25 |
| Talc, mg | 9 | 9 | 4.5 |
| Magnesium stearate, mg | 5 | 5 | 2.5 |
|  | 200 | 200 | 100 |

The above compositions have been tested for the delayed in vitro release with the following results:
I - in vitro release as measured with the apparatus Sartorium SM 16750

|  |  | Composition | | |
| --- | --- | --- | --- | --- |
|  |  | C | D | E |
| Release after | 1 hour | 21% | 20.7% | 24.5% |
| Release after | 2 hours | 35% | 33.6% | 44% |
| Release after | 3 hours | 48% | 52.5% | 61% |
| Release after | 4 hours | 60% | 61.5% | 76% |
| Release after | 6 hours | 75% | 77% | 90% |

EXAMPLE 3

The vincamine is granulated three times with a 40% Precirol solution in methylene chloride. The granulate, after sieving and drying, is admixed with calcium phosphate and kneaded with sorbitan (70% solution), talc and magnesium stearate. The mixture is then compressed to a weight of 300 mg:

|  | Composition F |
|---|---|
| Vincamine, mg | 50 |
| Precirol, mg | 30.8 |
| Calcium phosphate, mg | 158.7 |
| Sorbitan, mg | 47.5 |
| Talc, mg | 9 |
| Magnesium stearate, mg | 4 |
|  | 300 |

The in vitro release was measured with the apparatus Sartorium 16750:

| Release after | 1 hour | 21.4% |
|---|---|---|
| " | 2 hours | 38.9% |
| " | 3 hours | 64.9% |
| " | 4 hours | 73.4% |
| " | 6 hours | 92.5% |
| " | 8 hours | 105.7% |

(the last figure being well within the measurement limits of the apparatus).

In order to evaluate the absorption properties of the therapeutic composition of the invention, for three types of tablets, respectively containing 25, 50 and 75 mg, of the active substance, the hematic levels have been determined in vivo, after administration of the three compositions (C, D and E), in comparison with like compositions of the normal release type.

To this end 5 healthy voluntaries, 20 to 45 years aged, have been orally administered with a single unit dose.

In the following table the average values (± standard error) of the resulting hematic levels of vincamine are reported.

It can be appreciated that the slow-release compositions of the present invention, in comparison with the compositions containing the same amount of active substance but of the normal (quick) release type, show a less pronounced peak but the total hematic levels are much more persistent in time (the drug is present even after 36 hours).

The maximum hematic level was furthermore delayed and in the form of a "plateau": in fact it can be observed only about 6 hours as from the administration, whereas the peak of the standard compositions occurs at about 3 hours as from the administration.

If, however, the hematic levels of therapeutic significance are considered (higher than 0.2 µg/ml), it can be seen that these values are never attained in the case of composition E (which is of the delayed-release type), whereas these concentrations are obtained and exceeded in the case of compositions D (50 mg) and C (75 mg). More particularly, it is noteworthy that for both compositions C and D, the therapeutically active time range is from 45 minutes to 24 hours, whereas in the case of the corresponding normal release compositions therapeutically effective levels are present only up to 12 hours as from the administration. In view of the foregoing it can not only be appreciated that the compositions of the present invention show a more prolonged action, but also that the therapeutic advantages outlined above are yet achieved with unit dosages of not less than 50 mg.

Hematic values (µg/ml) of Vincamine after administration of normal (K) and prolonged release formulation (C, D, E) in 5 healthy voluntaries. (Means ± S.E. of 5 values).

| composition | time 0' | 0.5h. | 1h. | 2h. | 4h. | 8h. | 12h. | 24h. | 36h. |
|---|---|---|---|---|---|---|---|---|---|
| mg. 75 K | — | 0.386 ±0.0934 | 0.621 ±0.0357 | 0.837 ±0.0632 | 0.824 ±0.0941 | 0.516 ±0.0731 | 0.306 ±0.0245 | 0.058 ±0.0041 | — |
| C | — | 0.123 ±0.0034 | 0.384 ±0.0128 | 0.416 ±0.0271 | 0.546 ±0.0395 | 0.561 ±0.0426 | 0.484 ±0.0482 | 0.375 ±0.0125 | 0.120 ±0.0024 |
| mg. 50 K | — | 0.262 ±0.0713 | 0.412 ±0.0356 | 0.560 ±0.0541 | 0.550 ±0.0395 | 0.354 ±0.0451 | 0.210 ±0.0127 | 0.039 ±0.0027 | — |
| D | — | 0.106 ±0.0013 | 0.265 ±0.0121 | 0.315 ±0.0234 | 0.387 ±0.0241 | 0.393 ±0.0372 | 0.321 ±0.0349 | 0.236 ±0.0099 | 0.080 ±0.0012 |
| mg. 25 K | — | 0.127 ±0.0214 | 0.210 ±0.0013 | 0.279 ±0.0196 | 0.277 ±0.0241 | 0.177 ±0.0199 | 0.100 ±0.0101 | 0.019 ±0.0013 | — |
| E | — | — | 0.120 ±0.0016 | 0.164 ±0.0085 | 0.195 ±0.0106 | 0.208 ±0.0110 | 0.165 ±0.0081 | 0.102 ±0.0021 | 0.030 ±0.0011 |

What I claim is:

1. In the method for the treatment of cerebral circulatory diseases by oral administration of vincamine, the improvement consisting in administering vincamine in the form of a delayed-release formulation containing 50 to 75 mg of vincamine per unit dosage, in order to maintain in a hunam patient:
   (a) a hematic concentration of 0.1–0.3 µg/ml, when the metabolic effect is desired; and
   (b) a hematic concentration of 0.2–0.5 µg/ml, when a central vasodilating action is requested.

2. A method according to claim 1, wherein the delayed-release formulation is administered so as to maintain the hematic level to a constant value of at least 0.2 µg/ml.

3. A pharmaceutical composition for the treatment of cerebral circulatory diseases in the form of a delayed-release formulation, with a vincamine content per unit dosage of 50 to 75 mg, together with suitable carriers, and formulated so that there will be maintained in a human patient:
   (a) a hematic concentration of 0.1–0.3 µg/ml, when the metabolic effect is desired; and
   (b) a hematic concentration of 0.2–0.5 µg/ml, when a central vasodilating action is requested.

* * * * *

UNITED STATES PATENT AND TRADEMARK OFFICE
CERTIFICATE OF CORRECTION

PATENT NO. : 4,199,585
DATED : APRIL 22, 1980
INVENTOR(S) : VEGEZZI

It is certified that error appears in the above-identified patent and that said Letters Patent are hereby corrected as shown below:

On the title page insert

-- /73/ Assignee: Enrico Corvi Mora, Piacenza-Via Scalabrini, Italy --.

Signed and Sealed this

Nineteenth Day of August 1980

[SEAL]

Attest:

SIDNEY A. DIAMOND

Attesting Officer  Commissioner of Patents and Trademarks